United States Patent [19]

Suzuki et al.

[11] Patent Number: 4,791,930
[45] Date of Patent: Dec. 20, 1988

[54] COOLER FOR HUMAN TISSUE FOR USE DURING HYPERTHERMIA TREATMENT AGAINST CANCER

[75] Inventors: Hirosuke Suzuki, Tokorozawa; Satoru Kobayashi, Hitaka, both of Japan

[73] Assignee: Junkosha Co., Ltd., Tokyo, Japan

[21] Appl. No.: 543,109

[22] Filed: Oct. 18, 1983

[30] Foreign Application Priority Data

Oct. 25, 1982 [JP] Japan .................. 57-162214

[51] Int. Cl.⁴ .............................. A61F 7/00
[52] U.S. Cl. ............................ 128/399
[58] Field of Search ......... 128/303.1, 399–402, 128/7, DIG. 14; 264/340

[56] References Cited

U.S. PATENT DOCUMENTS

| | | | |
|---|---|---|---|
| 267,435 | 11/1882 | Leiter | 128/400 |
| 1,902,016 | 3/1933 | Copeman | 128/400 |
| 1,991,784 | 2/1935 | Bohenier et al. | 128/400 |
| 2,397,232 | 3/1946 | Barnes et al. | 128/399 |
| 3,859,986 | 1/1975 | Okada et al. | 128/7 |
| 4,082,893 | 4/1978 | Okita | 128/DIG. 14 |
| 4,149,541 | 4/1979 | Gammons et al. | 128/402 |
| 4,364,985 | 12/1982 | Tokuyama et al. | 264/340 |
| 4,397,314 | 8/1983 | Vaguine | 128/401 |

FOREIGN PATENT DOCUMENTS 1448068  9/1976  United Kingdom ........... 128/400

Primary Examiner—Max Hindenburg
Attorney, Agent, or Firm—Mortenson & Uebler

[57] ABSTRACT

A cooling device is provided for use in cooling surrounding human tissue during hyperthermia treatment of a cancerous tumor. The device comprises at least one tube constructed of a fluororesin having continuous pores, such as porous, expanded polytetrafluoroethylene, placed in a desired configuration adjacent the tissue to be cooled, and through which flows a coolant. Microwaves used in hyperthermia treatment of cancerous tumors can pass through the device and heat the tumor to be treated to a higher degree than heretofore possible because the adjacent noncancerous tissue can now be cooled. Because the tube is porous, the cooling effect is pronounced.

4 Claims, 2 Drawing Sheets

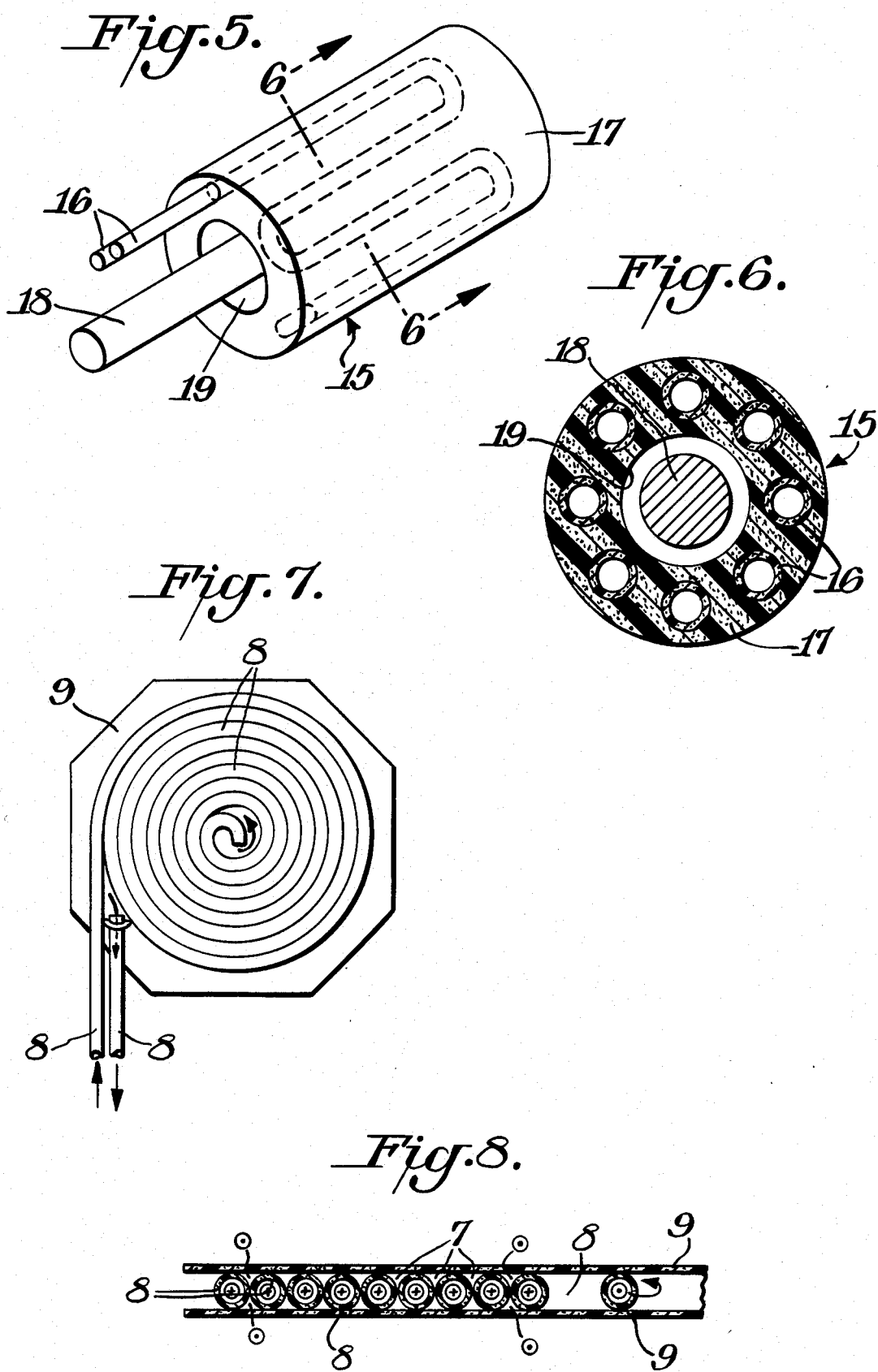

COOLER FOR HUMAN TISSUE FOR USE DURING HYPERTHERMIA TREATMENT AGAINST CANCER

BACKGROUND OF THE INVENTION

The present invention relates to a cooling device which is used to protect noncancerous regions during heat therapy treatment, called hyperthermic treatment, in which a cancerous region of a human is heated to 41–43° C. with heat producing microwaves to destroy the cancerous cells.

Conventional heat therapy for cancer of this kind is illustrated in FIG. 1, in which a heater such as a microwave antenna 2 is disposed on human epithelial tissue 1 to heat the cancerous region 4 of the cancerous organ 3 located deep in the human body up to temperatures of 41–43° C. The temperature in cancerous region 4 can be effectively measured with an apparatus as disclosed in Japanese Patent Application No. 151,848 entitled "Temperature Detecting Apparatus".

Unfortunately, in such therapy, the density of electromagnetic waves is highest just below the antenna 2, and the temperature in the region 4 should be kept constant. Therefore, the epithelial tissue 1 is higher in temperature than the cancerous region 4. Consequently, in the case of a relatively small cancerous region 4, this difficulty can be overcome by limiting the heat energy to a relatively low level. However, when the cancerous region 4 is large, it generally cannot be effectively cured.

Accordingly, it is an object of the present invention to provide a cooling device which is free from the foregoing shortcomings with the prior art, and which cools and protects noncancerous regions without decreasing the heating efficiency for effectively curing a cancerous tumor using microwave heating. This object is achieved in accordance with the present invention by constructing a cooling device for heat therapy for cancer such that the cooling device is disposed between a heater and a cancerous region to be cured and is provided with at least one tube through which a refrigerant is circulated, the tube consisting of a porous fluorocarbon resin having interconnecting pores.

SUMMARY OF THE INVENTION

A cooling device is provided for use in heat treatment of cancerous tumors, the cooling device being disposed between a microwave heater and a cancerous region to be cured, the cooling device including at least one tube through which a refrigerant is circulated, the tube consisting of a porous, expanded polytetrafluoroethylene resin having interconnecting pores. In a preferred embodiment, the tube is wound into a coil form, at least one side of the tube being held in place by a sheet of porous, expanded polytetrafluoroethylene having interconnecting pores. Both sides of the tube can be held in place by sheets of a porous, expanded polytetrafluoroethylene resin, and the peripheral portion of the coil of the tube can be placed in a liquid-tight relation with the sheets, the tube being centrally provided with a refrigerant inlet port and a refrigerant outlet port.

BRIEF DESCRIPTION OF THE DRAWINGS

FIG. 5 is a perspective view of still another cooling device of the invention.

FIG. 6 is a cross-sectional view of the device shown in FIG. 5 taken along the line 6—6 thereof.

FIG. 7 is a top plan view of a further embodiment according to the invention.

FIG. 8 is a cross-sectional view taken along line 8—8 of FIG. 7.

DETAILED DESCRIPTION OF THE INVENTION AND PREFERRED EMBODIMENTS WITH REFERENCE TO THE DRAWINGS

A cooling device is provided for use in cooling surrounding human tissue during hyperthermia treatment of a cancerous tumor. The device comprises at least one tube constructed of a fluororesin having continuous pores, such as porous, expanded polytetrafluoroethylene, placed in a desired configuration adjacent the tissue to be cooled, and through which flows a coolant. Microwaves used in hyperthermia treatment of cancerous tumors can pass through the device and heat the tumor to be treated to a higher degree than heretofore possible because the adjacent noncancerous tissue can now be cooled. Because the tube is porous, the cooling effect is pronounced.

According to the construction of the present invention, the walls of the tube through which a refrigerant is circulated has a large number of interconnecting pores. Therefore, when the internal fluid is liquid, the fluid is vaporized by heating and discharged through the wall of the tube, thus during the vaporizing of the fluid a large quantity of heat is removed and the required region can be effectively cooled. Further, since the portion through which refrigerant is circulated is made of a fluoroethylene resin, it has a small dielectric loss. The result is that the tube itself is not heated by electromagnetic waves and that the heating efficiency in the cancerous region to be heated is not lowered substantially.

In addition, according to the present invention, the portion through which refrigerant is circulated consists of a tube porous fluorocarbon resin having interconnecting pores. Hence the tube is flexible and inert to the human body. As the tube is made of inert material, the medical treatment can be undertaken without adversely affecting human tissue. It may occasionally be possible to embed the cooling device in the human body for a certain period for such treatment. Embodiments of the present invention will be described in detail with reference to FIGS. 2–5.

Figure 1:
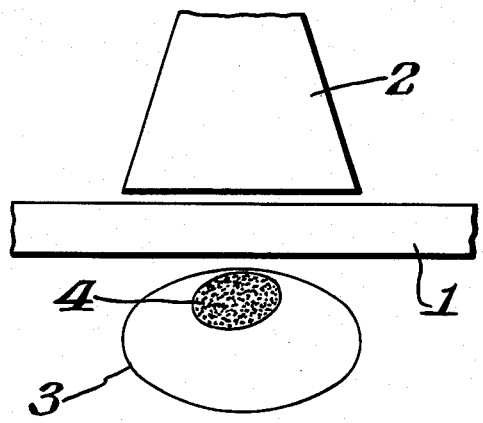
FIG. 1 is a conceptual view of conventional heat therapy for cancer.
Figure 2:
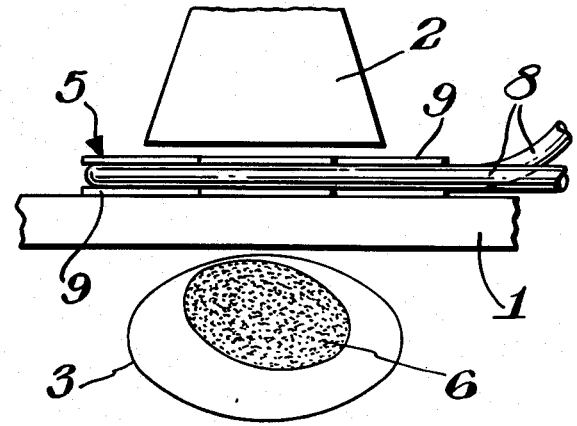
FIG. 2 is a conceptual view of heat therapy for cancer according to the present invention.

Referring to FIG. 2, there is shown a cooling device 5 embodying the concepts of the present invention. The device 5 is disposed between epithelial tissue 1 and microwave antenna 2 which acts as a heater. The device 5 is placed in direct contact with the tissue 1 and includes a tube 8 through which a refrigerant is circulated, the tube consisting of a porous fluorocarbon resin having interconnecting pores. Therefore, the cooling device is flexible and conforms to the epithelial tissue 1 and hence the device can effectively cool the tissue.

Further, since the device 5 is made of inert fluorocarbon resin, it does not give a feeling of uneasiness or physical disorder to the human body tissue 1.

In addition, since the portion of the cooling device 5 through which refrigerant is circulated has a great number of interconnecting pores, even if the refrigerant is warmed by the heater, the refrigerant is vaporized thereby and a large quantity of heat is removed, thereby cooling the tissue more effectively. Accordingly, even if a cancerous region 6 of cancerous organ 3, or the like, is hypertrophied, the required heat energy can be given to the cancerous region while cooling noncancerous regions effectively with the device 5. Consequently, the cancerous region 6 can be cured effectively.

Figure 3:
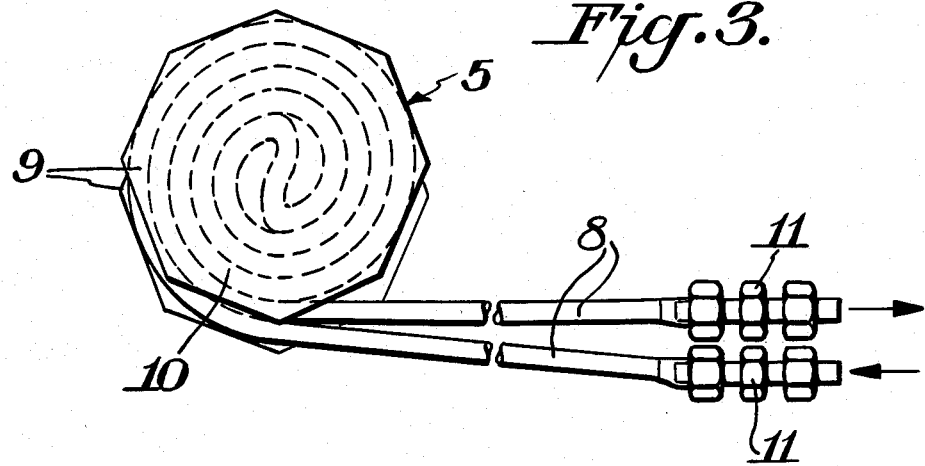
FIG. 3 is a perspective view of a cooling device of the invention.

Referring next to FIG. 3, an example of the cooling device 5 according to the invention is shown. The device 5 comprises a tube 8 consisting of porous, expanded polytetrafluoroethylene resin having interconnecting pores. The tube 8 is folded in two and wound into a coil form around the folded portion. The two sides of the coil can be held by sheets 9 of a porous fluorocarbon resin having interconnecting pores, whereby a portion 10 through which the refrigerant is circulated is formed. Both ends of the tube 8 are provided with couplings 11.

In the cooling device 5 of the above embodiment, the sheets 9 holding the coiled portion 10 through which the refrigerant is circulated have interconnecting pores. Therefore, if each of the sheets is in contact with the tube 8 at a point, the cooling due to the vaporization of refrigerant is not hindered. Although the coil is held by the sheets 9 on both sides of the above embodiment, it is also possible to mount one sheet 9 only one side of the coil. The tube 8 and the sheets 9 can be fabricated by the process disclosed in Japanese Patent Publication No. 18991/1976, for example.

Figure 4:
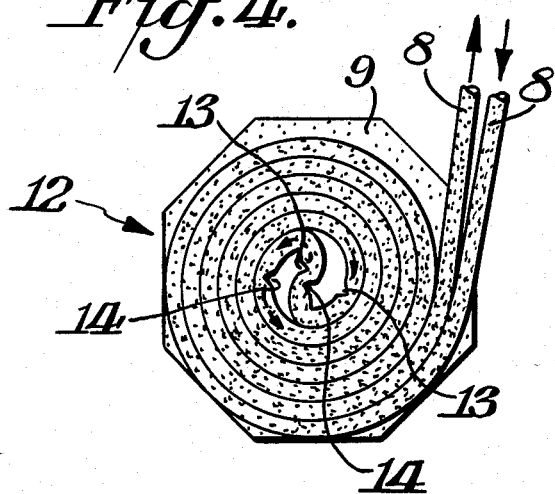
FIG. 4 is a fragmentary plan view of another cooling device according to the invention.
Figure 4A:
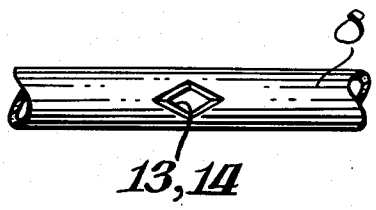
FIG. 4A is a fragmental side elevation of the tube used in the invention showing inlet/outlet ports 13/14.

FIG. 4 is a fragmentary plan view of another cooling device according to the invention, the device being indicated by reference numeral 12. The cooling device is similar to the cooling device having the coiled portion 10 shown in FIG. 3 except in the following respects. The tube 8 and the sheets 9 are held in liquid-tight manner by leaving no space between the neighboring turns, especially central turns, of the tube 8 made of porous, expanded polytetrafluoroethylene resin having interconnecting pores. The coil is centrally provided with a refrigerant outlet port 13 and a refrigerant inlet port 14. Thus, in the cooling device 12 of this example, the cooling capability in the center is enhanced to some extent and can be preferably used together with a heater, such as a microwave in which the heat energy density in the center is high.

Other kinds of cooling devices can be fabricated using the same cooling principles as the cooling device 12 shown in FIG. 4. Specifically, the following cooling device shown in FIGS. 7 and 8 is conceivable. A tube of a porous fluorocarbon resin having interconnecting pores is first prepared. Then, the tube is wound into a coil form around one end of the tube. The top and bottom surfaces of the coil are joined and held in liquid-tight manner by sheets of a porous fluorocarbon resin having interconnecting pores. The tube is used as a refrigerant inlet tube. A passage 7 is formed between the outer boundaries of the tube and the inner surfaces of the sheets and has a substantially triangular cross section such that the refrigerant discharged from the inner end of the tube returns through this passage. In this case, it is required that the end of the return passage in triangular form be provided with a refrigerant discharge tube as shown.

In the cooling device constructed as described just above, the return passage for the refrigerant can be a thin pipe having a triangular cross section and provided between the neighboring turns of the coil. Consequently, the velocity of the returning refrigerant is increased, and the area through which heat is dissipated is also enlarged. Further, the distance between the refrigerant and the object to be cooled is reduced, and the thermal resistance is decreased. In this manner, the cooling device can provide good cooling efficiency.

FIG. 5 is a perspective view of still another cooling device 15 according to the present invention. The device 15 is adapted to be inserted in a body cavity for curing a cancerous tumor produced in the cavity. The cooling device 15 comprises a tube 16 of porous, expanded polytetrafluoroethylene resin having interconnecting pores, the tube 16 being disposed overlapping on itself as shown. The tube is held in a cylindrical configuration of a body 17 of a porous fluoroethylene resin having interconnecting pores such that a heater, for example a microwave antenna 18, can be inserted in the center 19 of the cylinder.

In the embodiment described just above, the cooling device 15 is made of the porous fluorocarbon resin, and therefore it fits the internal wall of a body cavity or the region surrounding the embedded cooling device, permitting favorable cooling of noncancerous regions. Further, because it consists of inert fluorocarbon polymer, it gives no feeling of uneasiness or physical disorder to the region of the human body in which the device is inserted or embedded. Quite advantageously, this permits a stable and continuous treatment.

FIG. 6 shows a cross-sectional view of the device of FIG. 5 showing tube 16, cylindrical body 17 and microwave antenna 18 inserted into cavity 19.

As described thus far, in accordance with the present invention, a cooling device for heat therapy for cancer is provided which is disposed between a heater and a cancerous region to be cured, and which includes at least one tube through which a refrigerant is circulated, the tube consisting of a porous, expanded polytetrafluorocarbon resin having interconnecting pores. Thus, it is possible to cool noncancerous regions efficiently without substantially reducing the heating efficiency of the heater, so that the required heat energy is provided to the cancerous region, thereby attaining improved treatment. In addition, at least the portion of the cooling device through which a refrigerant is circulated consists of a tube of porous fluorocarbon resin having interconnecting pores. Hence, it is installed on the surface of the body or in a body cavity, thus leading to efficient cooling. Another advantage is that it results in no physical disorder to the human body. Furthermore, because the portion through which the refrigerant is circulated has a number of interconnecting pores, it can provide a large capability of cooling by virtue of the heat of vaporization of the refrigerant, in spite of the presence of the heater.

Suitable refrigerants include water and alcohol. Bonding between the porous tube and the porous sheets can be achieved by using suitable adhesives.

It is to be understood that the present invention is not limited to the foregoing embodiments but various changes and modification may be made therein without departing from the spirit and scope of the invention.

While the invention has been disclosed herein in connection with certain embodiments and detailed descriptions, it will be clear to one skilled in the art that modifications or variations of such details can be made without deviating from the gist of this invention, and such modifications or variations are considered to be within the scope of the claims hereinbelow.

What is claimed is:

1. A combination microwave heater and cooling device for use in heat treatment of cancerous tumors, the cooling device being disposed between said microwave heater and adjacent said cancerous region to be treated, the cooling device including at least one tube through which a refrigerant is circulated, the tube comprising a porous, expanded polytetrafluoroethylene resin having interconnecting pores.

2. A combination heater and cooling device for use in heat therapy for cancer as set forth in claim 1, wherein said tube is wound into a coil form, at least one side of the tube being held in place by a sheet of porous, expanded polytetrafluoroethylene having interconnecting pores.

3. A combination heater and cooling device for use in heat therapy for cancer as set forth in claim 1, wherein said tube is wound into a coil form and both sides of the tube are held in place by sheets of a porous, expanded polytetrafluoroethylene resin, and wherein the peripheral portion of the coil of the tube is placed in a liquid-tight relation with the sheets, the tube being centrally provided with a refrigerant inlet port and a refrigerant outlet port.

4. A combination heater and cooling device for use in heat therapy for cancer as set forth in claim 1, wherein said tube comprises:

a refrigerant inlet tube comprising a porous, expanded polytetrafluoroethylene resin having interconnecting pores, the inlet tube being wound in a coil, the center of said coil being one end thereof of said tube, said device having a pair of sheets of porous, expanded polytetrafluoroethylene resin have interconnecting pores, the sheets being joined to both sides of the coiled portion of the inlet tube in a liquid-tight manner to support the coiled portion, and a refrigerant output tube disposed at the end of the return path for the refrigerant, said return path being formed by the inlet tube and the sheets.

* * * * *